United States Patent [19]
Sertic et al.

[11] Patent Number: 5,116,316
[45] Date of Patent: May 26, 1992

[54] AUTOMATIC IN-LINE RECONSTITUTION SYSTEM

[75] Inventors: James L. Sertic, Portage, Mich.; Joseph A. Bancsi, Vernon Hills, Ill.; Lisa D. Sertic, Portage, Mich.; Grace M. Esche, Algonquin; John Lawson, McHenry, both of Ill.

[73] Assignee: Baxter International Inc., Deerfield, Ill.

[21] Appl. No.: 660,493

[22] Filed: Feb. 25, 1991

[51] Int. Cl.⁵ .............................. A61M 37/00
[52] U.S. Cl. ........................ 604/83; 604/123; 604/246
[58] Field of Search .................. 604/82–86, 604/56, 122, 123, 131, 65, 66, 67, 251, 252, 246

[56] References Cited

U.S. PATENT DOCUMENTS

| | | |
|---|---|---|
| 3,941,171 | 3/1976 | Ogle . |
| 4,410,321 | 10/1983 | Pearson et al. . |
| 4,411,662 | 10/1983 | Pearson . |
| 4,424,056 | 1/1984 | Urquhart et al. . |
| 4,432,755 | 2/1984 | Pearson . |
| 4,432,756 | 2/1984 | Urquhart et al. . |
| 4,439,183 | 3/1984 | Theeuwes . |
| 4,458,733 | 7/1984 | Lyons . |
| 4,465,471 | 8/1984 | Harris et al. . |
| 4,474,574 | 10/1984 | Wolfe et al. . |
| 4,479,793 | 10/1984 | Urquhart et al. . |
| 4,479,794 | 10/1984 | Urquhart et al. . |
| 4,525,162 | 6/1985 | Urquhart et al. . |
| 4,534,757 | 8/1985 | Geller . |
| 4,534,758 | 8/1985 | Akers et al. . |
| 4,548,599 | 10/1985 | Urquhart et al. . |
| 4,573,967 | 3/1986 | Hargrove et al. . |
| 4,581,014 | 4/1986 | Millerd et al. . |
| 4,589,867 | 5/1986 | Israel . |
| 4,623,334 | 11/1986 | Riddell . |
| 4,804,366 | 2/1989 | Zdeb et al. . |
| 4,850,978 | 7/1989 | Dudar et al. . |
| 4,936,829 | 6/1990 | Zdeb et al. ................ 604/85 |
| 5,024,657 | 6/1991 | Needham et al. ........... 604/56 X |

FOREIGN PATENT DOCUMENTS

| | | |
|---|---|---|
| 1173795 | 4/1984 | Canada . |
| 0059694 | 5/1982 | European Pat. Off. . |

Primary Examiner—John D. Yasko
Attorney, Agent, or Firm—Paul E. Schaafsma; Amy L. H. Rockwell; Paul C. Flattery

[57] ABSTRACT

The present invention provides a system for automatically reconstituting a drug in-line and delivering the drug to a patient. Pursuant to the present invention, a system is provided that allows fluid entry into a vial, that houses the drug to be reconstituted, with concurrent air elimination. Mixing via different fluid entry levels is provided. Due to the unique fluid flow path of the present invention reconstitution of the drug is ensured. The system, method, and apparatus of the present invention can be utilized with a computer controlled pump. When so utilized, a completely automated procedure can be achieved.

23 Claims, 3 Drawing Sheets

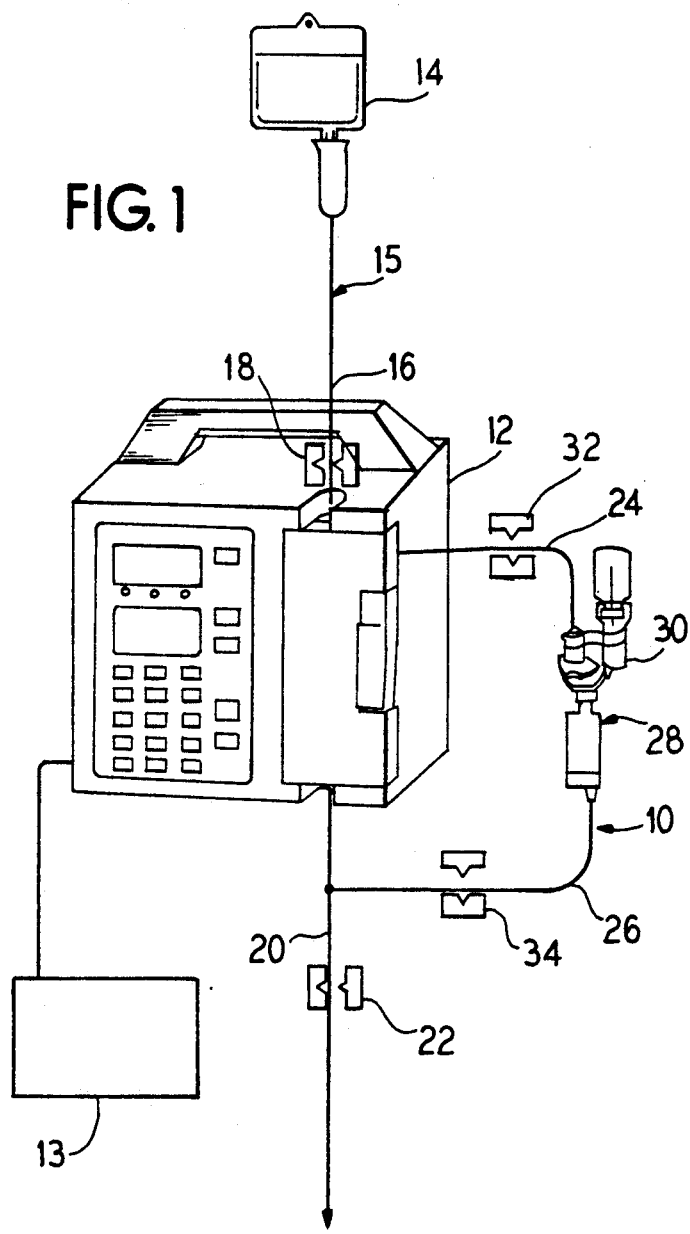
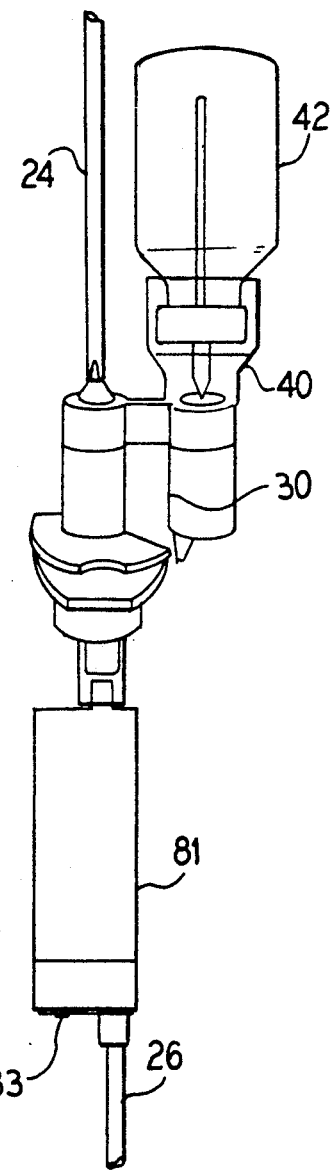

AUTOMATIC IN-LINE RECONSTITUTION SYSTEM

BACKGROUND OF THE INVENTION

The present invention relates to the administration of a drug or other beneficial agent to a patient. More specifically, the present invention relates to the administration of a reconstituted drug or beneficial agent with a diluent to a patient.

For many applications, drugs may be mixed with a diluent before delivery to a patient. For example, it is known to mix certain drugs, prior to intravenous delivery, with a diluent such as a dextrose solution, saline solution, or even water.

It is also known, to store drugs in a powdered state and then reconstitute the drug prior to using same. For example, certain drugs can be stored for much greater periods of time if they are stored in a powder, dry, form. The drugs can be reconstituted prior to use. One method for reconstituting a drug is to utilize a syringe to inject liquid into a vial for mixing. The syringe can eventually withdraw the mixed solution from the vial.

When a drug must be diluted before delivery to a patient the drug is often injected into a container of diluent, if necessary, after it is reconstituted. The container can be connected to an administration set for delivery to a patient. For example, the diluent can be packaged in a glass bottle, or flexible plastic container such as are sold under the names MINI-BAG ™ and VIAFLEX ® by Baxter Healthcare Corporation of Deerfield, Ill. These containers have administration ports for connection to an administration set which delivers the contents of the container from the container to the patient. The drug is typically added to the container through an injection site on the container.

Drugs may be packaged separately from the diluent for various reasons. Many drugs do not retain their chemical and physical stability when mixed with a diluent. Thus, the drugs and diluent cannot be stored for a substantial period of time. Additionally, for commercial reasons, drugs are often packaged separately from the diluent because many companies which manufacture drugs are not engaged in the business of providing medical fluids in containers for intravenous delivery, and vice versa.

Therefore, it is a common practice that medical personnel must mix a drug and diluent. However, this presents a number of problems.

The reconstitution procedure is time consuming and requires aseptic technique. Often it is difficult to reconstitute the drug because the powdered drug is "caked" at the bottom of the vial. Thus, when liquid is injected into the vial from a syringe in an attempt to reconstitute the drug, the surface area of contact between the liquid and the powdered drug may initially be quite small, making the mixing procedure even more time consuming.

Because of the limited vial volume, the increasing drug concentration in the diluent makes it harder to finish the reconstitution process. The operator may attempt to solve this problem by repeatedly injecting solution into the vial, mixing and withdrawing the solution. But, this requires many additional injections and movement of the syringe within the vial which increase the likelihood of contamination. Also, it is sometimes difficult to get all of the drug and/or liquid out of the vial, thus increasing the time required to perform the reconstitution procedure.

The reconstitution procedure should preferably be performed under sterile conditions. This requirement also makes the reconstitution procedure more arduous and time consuming: sterile conditions are often hard to maintain. In some instances, a laminar flow hood may be required under which the reconstitution procedure is performed.

Some drugs, such as some chemotherapy drugs, are toxic. Exposure of the operator to the drugs during reconstitution may be dangerous, especially if the operator works with such drugs on a daily basis and is repeatedly exposed to them.

After a drug is reconstituted and withdrawn into a syringe barrel, the drug may in some instances be injected immediately into the intravenous system of a patient. More typically, however, the reconstituted drug is injected from the syringe into a larger container of solution as discussed above, for connection to an intravenous administration set.

It is typically necessary to add the reconstituted drug in the syringe to a larger volume of fluid because often the reconstituted drug in the syringe is still at a sufficiently high concentration as to cause local toxicity in the veins of a patient near the injection site where the needle pierces the skin. This can create severe vein irritation which can be harmful to the patient.

Additionally, even though the proper dose of medication is in the syringe, immediate injection into the patient's blood stream can create a condition of systemic toxicity wherein the level of drug concentration in the patient's entire blood stream is dangerously high. Additionally, injection from the syringe directly into the patient requires an additional injection into the patient, which can be painful for the patient and provides another opportunity for infection.

For these reasons, the reconstituted drug is more typically injected into a diluent container.

A patient is typically administered a dextrose or saline solution from a large volume parenteral container, for example, such as a one liter container, delivered through an administration set such as a CONTINU-FLO ® administration set sold by Baxter Healthcare Corporation. If the reconstituted drug were injected into such a large volume parenteral container, delivery of the drug would usually be made over too long a time period. Often, these large volume fluids are delivered at very slow flow rates.

It is also known to inject the reconstituted drug into a small volume parenteral container, such as a fifty milliliter container sold by Baxter Healthcare Corporation. This MINIBAG ™ container is then supported at a higher elevation than a larger volume parenteral container and is connected by a secondary administration set to an injection site on the primary administration set. Because it is maintained at a higher elevation, the reconstituted drug in the small volume container is delivered, after which fluid from the large volume container begins to flow once more. By utilizing a small volume container connected to an administration set for delivery of the drug or other beneficial agent, instead of a direct syringe injection, the drug is delivered over a preferred time period that tends to minimize negative side effects.

Reconstitution and drug delivery systems are also known. A closed reconstitution delivery system is disclosed in U.S. Pat. No. 4,410,321; U.S. Pat. No.

4,411,662; U.S. Pat. No. 4,432,755; and U.S. Pat. No. 4,458,733, all assigned to Baxter International Inc., the assignee of the present invention. As shown therein, a container includes a drug and a diluent in separate compartments which are reconstituted in a closed system before the drug is delivered to the patient. Typically, the container is connected to an administration set which is connected at its other end to the primary administration set, such as with the small volume parenteral container described above. The container shown in these patents solves many of the problems associated with syringe reconstitution. The product does, however, necessitate a series of reconstitution steps which must be performed by the nurse or other operator prior to delivering the fluid from the container.

U.S. Pat. No. 4,424,056; U.S. Pat. No. 4,432,756; U.S. Pat. No. 4,439,183; U.S. Pat. No. 4,474,574; U.S. Pat. No. 4,479,793; U.S. Pat. No. 4,479,794; U.S. Pat. No. 4,525,162; and U.S. Pat. No. 4,548,599 and Canadian Patent No. 1,173,795, assigned to Alza Corporation of Palo Alto, California disclose a parenteral delivery system which has a formulation chamber therein for administering a beneficial agent such as a drug. The system provides for reconstitution of the drug by fluid flowing from a large volume parenteral container for example, through the administration set containing the formulation chamber with the drug therein.

Another passive reconstitution system is disclosed in European Patent Application No. 0059694 to Aktiebolaget Hassle of Sweden.

Still another device for delivering a drug "in-line", i.e., in the administration set, is disclosed in U.S. Pat. No. 4,534,757 assigned to Alza Corporation. The device holds the drug and includes a section through which the liquid passes in a direction substantially opposite to the general direction in which liquid flows to the patient.

Yet another system which attempts to provide for drug reconstitution in-line without manual reconstitution by a nurse or other operator is shown in U.S. Pat. No. 4,465,471, assigned to Eli Lilly and Co. of Indianapolis, Indiana. That patent discloses constructions for a receptacle in the administration set itself. A separate cartridge containing the drug to be reconstituted and delivered to the patient is plugged into the receptacle.

European Patent Application Publication No. 0146310 to Eli Lilly and Co., corresponding to U.S. Pat. No. 4,573,967, is directed to a system for drug reconstitution including an intravenous administration set and a drug vial and utilizes a vial vacuum to reconstitute the drug.

U.S. Pat. No. 4,534,758 to Akers et al. discloses a relatively complex drug delivery apparatus with various valves. When liquid from a container is delivered to the drug vial, the vial is to be agitated for a time sufficient to suspend the previously dry medicine.

U.S. Pat. No. 4,581,014 to Millerd et al., assigned to Ivac Corporation of San Diego, California discloses a selector valve for delivering a previously reconstituted drug from a drug vial through an intravenous administration set to a patient.

All the publications described above are directed to solutions to the time consuming reconstitution procedure and/or its associated problems, such as delivery of the solution to a patient. In most of the offered solutions, delivery of the drug is intended to be passive, i.e., once the drug is placed into the administration set, manual reconstitution steps are not required.

Israel U.S. Pat. No. 4,589,867 discloses a delivery apparatus including an integral diluent container and a mixing container with an upward flow path.

Ridell U.S. Pat. No. 4,623,334 discloses delivery of a drug from an add-on vial. Israel and Riddell are principally directed to delivering liquid having a decreasing drug concentration over time, to a patient.

Ogle U.S. Pat. No. 3,941,171 is directed to a fluid transfer device including an adapter for connecting a chamber having a pierceable closure with another container.

Still another common feature of many of the attempted solutions disclosed in these publications is that delivery of the drug is intended to be able to be made in a manner which is essentially independent of the fluid flow rate through the administration set and into the patient. Stated differently, some of the systems are designed to deliver a certain dosage of drug in a preselected time period, within a broad range of fluid flow rates. Delivery of a drug independent of flow rate is desirable because it ensures that the necessary dosage will be delivered within a therapeutically acceptable time period, which may be typically about twenty to thirty minutes, although this time period may vary depending upon the drug and dosage.

By making delivery of the drug or other beneficial agent independent of the flow rate, the system ensures that the drug will not be delivered too quickly should the flow rate be set too high by the nurse or other operator, thereby preventing the problem of systemic toxicity discussed above.

Some of the documents, such as U.S. Pat. No. 4,424,056; U.S. Pat. No. 4,479,793; and U.S. Pat. No. 4,479,794 are also directed to systems having a beneficial agent placed "in-line" in an administration set for mixing of the agent and delivery to a patient, wherein the delivery of the agent may be made in a given volume of fluid. Also, a valve controlling fluid flow may be manually operated to deliver the agent in a manner which can be made dependent upon fluid flow.

U.S. Pat. No. 4,850,978 discloses a system that includes a cartridge for introducing a beneficial agent into a fluid conduit for delivery of the agent to a patient. The cartridge includes a rigid hollow tube and an agent-containing chamber slidably mounted at least partially within the hollow tube. In a first, pre-use position, the chamber extends farther from the hollow tube than it does in a second position. A cannula is mounted to the hollow tube extending opposite the chamber. When the chamber is in the second position, the cannula pierces the closure means creating a fluid flow path.

U.S. Pat. No. 4,804,366 also discloses a drug delivery system including an adapter having an improved flow path means provided both at an inlet and an outlet to the agent-containing chamber of a cartridge. The cartridge and adapter permit a single opening through the injection sites at opposite ends of the flow path means, while still permitting simultaneous flow both into and out of the chamber. An adapter and a cartridge is provided, including a rigid cannula with an inlet and an outlet in a shell substantially coaxial with and spaced from the cannula intermediate of the cannula inlet and the cannula outlet so that the shell of the cannula define a channel therebetween. Both the cannula inlet and the cannula outlet are adaptable to form a single piercing opening in a resilient injection side associated with the receptacle of the delivery system. Both the channel outlet and channel inlet are adapted to form a single piercing opening in a resilient injection site associated with the cartridge.

SUMMARY OF THE INVENTION

The present invention provides a means for automatically reconstituting a drug in-line and delivering the drug to a patient. Pursuant to the present invention, a system is provided that allows fluid entry into a vial, that houses the drug to be reconstituted, with concurrent air elimination. Mixing via different fluid entry levels is provided. Due to the unique fluid flow path of the present invention reconstitution of the drug is ensured. Delivery of the fluid from the vial is provided with concurrent air reentry into the vial.

The system, method, and apparatus of the present invention can be utilized with a computer controlled pump. When so utilized, a completely automated procedure can be achieved.

To this end, a system for adding a beneficial agent to a fluid to be administered to a patient is provided that comprises a vial including an agent and a fluid source. The fluid source is coupled to a first fluid line. An access site is provided including means for coupling the vial to the access site and providing at least two separate fluid paths between the access site and an interior of the vial. The access site includes means for allowing fluid to enter the vial from a first fluid path and allowing air to be vented from the vial through a second fluid path. The access site also includes means for allowing fluid to enter the vial through the second fluid path and exit the vial through the first fluid path. A tubing segment to allow fluid exiting the vial to be administered to a patient is also provided. Additionally, the system includes a pump for assisting fluid flow through the system.

Preferably, the system includes valves for regulating fluid flow through at least portions of the system. Preferably, the system includes a filter located at an end of the access site.

In an embodiment, the means for coupling the vial to the access site includes an adapter having means for allowing fluid to enter the vial including a rigid cannula having an inlet and an outlet and a shell spaced from the cannula intermediate of the cannula inlet and the cannula outlet, with the cannula and the shell defining a channel therebetween, about the exterior of the cannula, the channel including a channel inlet short of the cannula outlet and a channel outlet short of the cannula inlet. The channel outlet and the cannula inlet are both adaptable to pierce a single opening in the vial.

In an embodiment, the present invention provides a system for adding a beneficial agent to a fluid to be administered to a patient. The system comprises a vial including an agent, a fluid source, and an access site for adding an agent to the fluid. Four tubing segments are provided. A first tubing segment is connected to the fluid source. A second tubing segment is connected to the first tubing segment and an end of the access site. A third tubing segment is connected to an end of the access site and to a fourth tubing segment. The fourth tubing segment, integral with the first tubing segment, is connected to an end of the third tubing segment and is in fluid communication with the patient. An adapter for allowing a vial to be coupled to the access site and establishing two fluid flow paths into and out of the vial is provided. A pump located between the first and fourth tubing segment assists in fluid flow through the system. Valves are provided that regulate fluid flow through each of the tubing segments.

The system is so constructed and arranged that fluid flows into the vial from the third and fourth tubing segments and out of the vial into the second tubing segment.

The present invention also provides a method for delivering an agent to a patient.

In an embodiment, the method comprises the steps of: coupling a vial including an agent to a system for delivering fluid from a fluid source to a patient; causing fluid from the fluid source to enter the vial, from an adapter that provides at least two additional fluid paths between the adapter and the vial and provides fluid communication between the vial and an access site, the fluid entering the vial from a first of said fluid paths and the second fluid path allowing air to be vented from the vial; causing fluid to enter the vial from the second fluid path in the adapter; causing fluid to exit the vial from the first fluid path in the adapter; and delivering the fluid that exists the vial to a patient.

Preferably, as the fluid exits the vial, air enters the vial from the second fluid path.

The fluid is caused to enter the vial from the fluid source by gravity or preferably assisted by pumping.

Preferably, a pump is used to cause at least some of the fluid to flow through at least one of the fluid paths.

Preferably, an air vent is provided in the system, and air that is caused to exit the vial is vented through the air vent.

In an embodiment of the present invention, a method for reconstituting a drug is provided that comprises the steps of: providing a fluid source coupled to a first fluid line; providing a second fluid line, one end of which is in fluid communication with an upper portion of the first fluid line and a second end of which is in fluid communication with an end of an access site; providing a third fluid line, one end of which is in fluid communication with a lower portion of the first fluid line and a second end of which is connected to an end of the access site; providing a pump that acts on a portion of the first fluid line; providing first, second, third, and fourth valves, the first valve regulating fluid flow through the first fluid line upstream of the pump, the second valve regulating fluid flow within a portion of the second fluid line, the third valve regulating fluid flow within a portion of the third fluid line, and the fourth valve being located downstream of the pump and regulating fluid flow through the portion of the first fluid line located downstream of the pump; providing an adapter including means for providing two fluid inlet paths and two fluid outlet paths; coupling a vial including a drug to be reconstituted to the adapter; closing the fourth valve while opening the first, second, and third valves and allowing fluid to fill the vial by gravity; closing the first and fourth valves while opening the second and third valves and causing the pump to act on the first tube segment to cause fluid to be pumped; closing the first and third valves and opening the second and fourth valves causing fluid to drain from the vial; and after the vial has drained closing the second and third valves and opening the first and fourth valves allowing fluid to be delivered from the fluid source.

The present invention provides many advantages over prior art devices. Time-intensive manual reconstitution is not required pursuant to the present invention. Further, a direct delivery from a vial is provided immediately upon reconstitution of the vial. This is especially beneficial for use with drugs that are unstable in liquid form.

Additionally, an advantage of the present invention is that end of dose indication is provided.

Further, an advantage of the present invention is that a smooth drug delivery profile is achieved by the present invention.

As compared to a passive system, an advantage of the present invention is that a better mixing is provided because fluid initially enters at the bottom of the vial and then enters at the top of the vial providing a better mixing within the vial.

Still further, an advantage of the present invention is that it does not require repriming for multi-dosing because air elimination is automatic.

Additionally, an advantage of the present invention is that is provides the potential for micro-dosing.

Moreover, an advantage of the present invention is that it allows one to vary the drug delivery profile.

A further advantage of the present invention is that it can be used to administer reconstituted drugs to fluid-restricted patients.

Additional features and advantages of the present invention are described in, and will be apparent from, the detailed description of the presently preferred embodiments and from the drawings.

BRIEF DESCRIPTION OF THE DRAWINGS

FIG. 1 illustrates an exploded perspective view of an embodiment of the present invention;

FIG. 2 illustrates an enlarged perspective view of a portion of the present invention;

DETAILED DESCRIPTION OF THE PRESENTLY PREFERRED EMBODIMENTS

Figure 3:
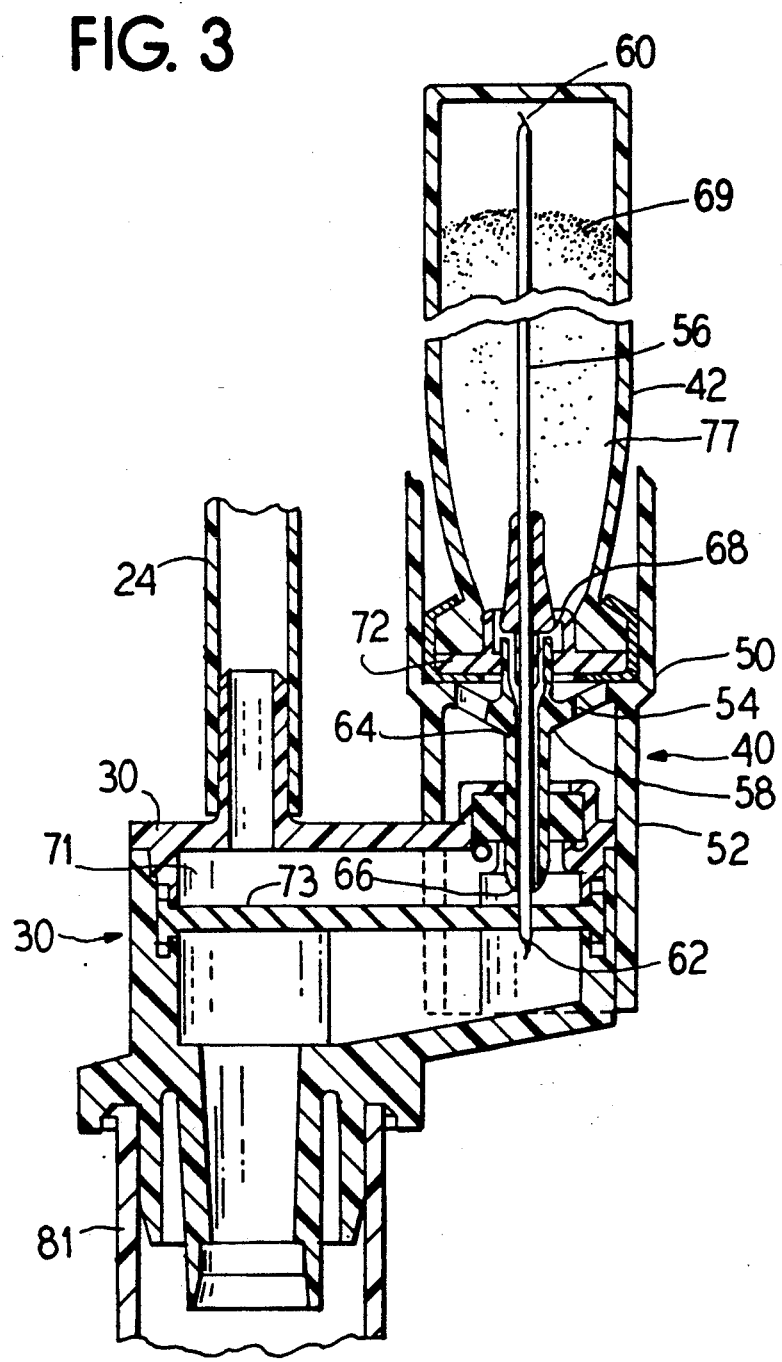
FIG. 3 illustrates a cross-sectional view of portions of the apparatus illustrated in FIG. 2.

The present invention provides an automatic in-line reconstitution system. The in-line reconstitution system is specifically adapted to provide a means for reconstituting a powdered drug, or adding a diluent to a drug. An automatic system is provided that has many advantages over prior devices. Pursuant to the present invention, an automatic system is provided including means for providing fluid entry from a first fluid path into a vial containing the drug, with concurrent air elimination through a second fluid path. Mixing is achieved by allowing fluid to also enter the vial from the second fluid path and exit the vial from the first fluid path. Concurrent air re-entry into the vial is also provided.

Referring now to FIG. 1, an embodiment of the reconstitution device and system 10 of the present invention is illustrated. As illustrated, preferably the system 10 of the present invention includes a pump 12. As discussed in more detail hereinafter, the pump 12, that is preferably controlled by a computer 13, allows the present invention to provide a completely automated reconstitution system 10. To this end, in a preferred embodiment the pump is a parenteral pump marketed by Baxter Healthcare Corporation under the trademark FLO-GARD® 6200.

As illustrated, the system of the present invention includes a fluid source 14 that is in fluid communication with a first tubing segment 15. The fluid source 14 can be a parenteral container of a diluent such as a dextrose or a saline solution.

The first tubing segment 15 includes an upper portion 16 and a lower portion 20. A first valve 18 is provided and is located upstream from the pump 12. The first valve 18 regulates fluid flow from the fluid source 14 through the upper portion 16 of first tubing segment 15 to the pump 12.

As illustrated in FIG. 1, located downstream from the pump 12 is the lower portion 20 of the first tubing segment 15. The lower portion 20 of the first tubing segment 15, is contiguous with the upper portion 16 of the first tubing segment 15 and is preferably the same tube. It should be noted that in FIG. 1, the portion of first tubing illustrated as being within the pump 12 is that portion of the tubing that is acted upon by the pump 12. Accordingly, when the first valve 18 is opened, and the pump 12 is operating, the pump will pump fluid from the fluid source 14 to the lower portion 20 of the first tubing segment 15.

Located downstream of the pump 12 is a fourth valve 22. The fourth valve 22 regulates fluid flow through the lower portion 20 of the first tubing segment 15 and ultimately, therefore to the patient.

A second tubing segment 24, that cooperates with a third tubing segment 26 to create a tubing loop 28, is provided. The second tubing segment 24 extends, in fluid communication, from the upper portion 16 of the first tubing segment 15 to an access member 30. As discussed in more detail hereinafter, the access member 30 allows a drug to be reconstituted and then delivered to a patient. A second valve 32 is provided that regulates fluid flow through the second tubing segment 24. The second valve 32 regulates fluid flow therefore between the upper portion 16 of the first tubing segment 15 and the access member 30.

The third tubing segment 26 extends from an end of the access member 30 to the lower portion of the first tubing segment 15. A third valve 34 is provided to regulate fluid flow between the access member 30 and the lower portion 20 of the first tubing segment 15.

Figure 4:
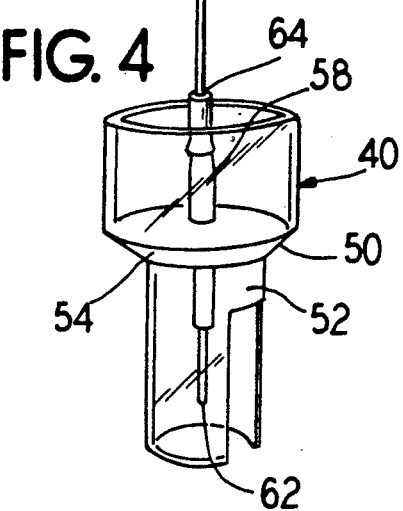
FIG. 4 illustrates an embodiment of the adapter of the preset invention.

Referring now specifically to FIGS. 2, 3, and 4, the access member 30, adapter 40, and vial 42 are illustrated. The adapter 40 is similar to that set forth in U.S. Pat. No. 4,850,978 and U.S. Pat. No. 4,804,366 the disclosures of which are incorporated herein by reference.

The adapter 40 allows the vial 42 to be connected to the access member 30. As discussed in more detail hereinafter, the adapter 40 and access member 30 cooperate to allow the drug in the vial 42 to be reconstituted and administered to a patient.

Briefly, the adapter 40 includes a rigid hollow cylinder or tube means 50 and a keyway wall 52, the keyway wall being a part of the tube 50. A plate 54 is mounted across the tube and defines the starting point of the keyway wall.

A cannula 56 extends through the plate 54. A generally cylindrical shell 58 extends from both sides of the plate 54. The hollow tube 50, the plate 54, and the shell 58 may all be formed as a single piece of the same material such as a plastic.

The shell 58 is spaced from the cannula 56 with the shell 58 encompassing the cannula 56 but being shorter than either end of the cannula 56. The cannula 56 includes an inlet 60 and an outlet 62. The inlet 60 and outlet 62 preferably are pointed to facilitate piercing. Alternatively, a blunt cannula and preslit injection site can be utilized.

The shell 58 is intermediate of the cannula inlet and outlet 60 and 62, respectively. The cannula 56 and the shell 58 define a channel 64 therebetween. In a preferred embodiment, the periphery of the cannula 56 is circular along its length. Similarly, the internal surface of the shell 54 is preferably arcuate and preferably circular along its length.

The channel 64 includes a channel inlet 66 defined between the shell 58 and the cannula 56, short of the cannula outlet 62. Similarly, the channel 64 includes a channel outlet 68 defined by the shell 58 and the cannula 56, short of the cannula inlet 66.

The cannula 56 is secured to the shell 58 while still maintaining an open flow path through the channel inlet 66, the channel 64, and the channel outlet 68. Thus, a very small flow path is created outside of a single cannula 56, with precision.

As illustrated, a vial 42 is provided for containing a beneficial agent 69 such as a dry powdered drug, although the agent may also be a liquid. A pierceable stopper 72 or other closure means closes the vial 42.

The shell 58, along with the channel outlet 68 and the cannula inlet 60, are designed to pierce the pierceable stopper 72 or other injection site/closure means to the vial 42 having the beneficial agent therein. Similarly, as discussed in more detail hereinafter, the shell 58 along with the channel inlet 66, together with the cannula outlet 62, are designed to pierce the access member 30.

In use, the adapter 40, vial 42, and access member 30 function as follows:

Upon engagement of the adapter 40 and vial 42 as illustrated in FIG. 3, liquid flowing into the access member 30 at an inlet 71 is prevented from passing through the through-bore and out the access member 30 because the resilient divider 73 has been sealed about the cannula outlet 62 portion at the through bore. Thus, liquid entering the access member 30 enters the channel inlet 66, flows through the channel 64 and enters the interior 77 of the vial 42 at the channel outlet 68.

As liquid rises within the vial 42, residual air within the vial 42 is forced downstream through the cannula inlet 60 and then the cannula outlet 62. Due to the construction of the access member 30, the air enters a filter 81 of the access member 30 and is expelled through an air vent 83. To this end, the filter 81 preferably is a hydrophobic/hydrophilic filter. An Endure filter has been found to function satisfactory in this regard.

As discussed in more detail hereinafter, the system 10 of the present invention is constructed so that liquid can also enter the vial 42 through the cannula 56 and exit the vial 42 through the channel 58 providing a fluid flow ensuring reconstitution of the drug.

Liquid exiting the vial 42 has an appropriate concentration of beneficial agent mixed therewith of delivery to the patient. The flow path created within the vial 42 by the system creates a density gradient within the vial 42 such that the concentration of drug within the liquid exiting at the channel will not be so high as to create local toxity to the patient. Likewise, the dual fluid flow path into the vial 42 creates a flow system that ensure that substantially all of the drug is reconstituted.

The reconstitution system 10 of the present invention provides an improved method for reconstituting a drug. Specifically, the present invention provides an automatic reconstitution method and system. To this end, four principal cycles are utilized in the method of the present invention.

Initially there is a fill cycle. After the vial 42 is fitted onto the adapter 40 and the adapter 40 is docked on the access member 30, valve 22 is then closed while valves 18, 32, and 34 are open. The pump 12, such as a FLO-GARD® 6200, is then stopped. Due to gravity, fluid fills the vial 42 through the opening created at the bottom of the inverted vial through the channel 64. Air is then forced through the cannula 56 at the top of the inverted vial and exits the access member 30 through the filter 81.

The second step in the cycle is the mix cycle. Valves 32 and 34 are opened and valves 18 and 22 are then closed. The pump 12 is then started at a specific rate, for example, 999 ml/hour. Fluid travels through the pump 12 and the tubing loop. Fluid enters the vial 42 now through the cannula 56 at the top of the inverted vial 42. Fluid exits the vial 42 at the bottom of the inverted vial 42 through the channel 64. This results in most of the interior surface, of the vial 42, being wetted using the variable fluid entry system set forth herein.

In the third step of the cycle, the vial 42 is drained. To this end, valves 18 and 34 are closed and valves 22 and 32 are opened. The rate on the pump reverts to the program primary rate. Fluid drains from the vial 42 and air bubbles up through the filter to replace the fluid that is drained through the vial.

In the fourth step of the cycle, primary delivery is provided. When the vial 42 has emptied, valves 32 and 34 are closed and valves 18 and 22 are open. The fluid is then delivered from the primary solution container 14 as normal.

The utilizing a computer control pump 12 such as the FLO-GARD® 6200, the entire system can be automated. To this end, the valves 18, 22, 32, and 34 can be controlled by the computer controlled pump 12 and the user merely enters the vial size, fill time, mix time, and drug name either on the keyboard or through and optional bar code reader. The pump 12 can then sequence the necessary reconstitution sequence.

Figure 5:
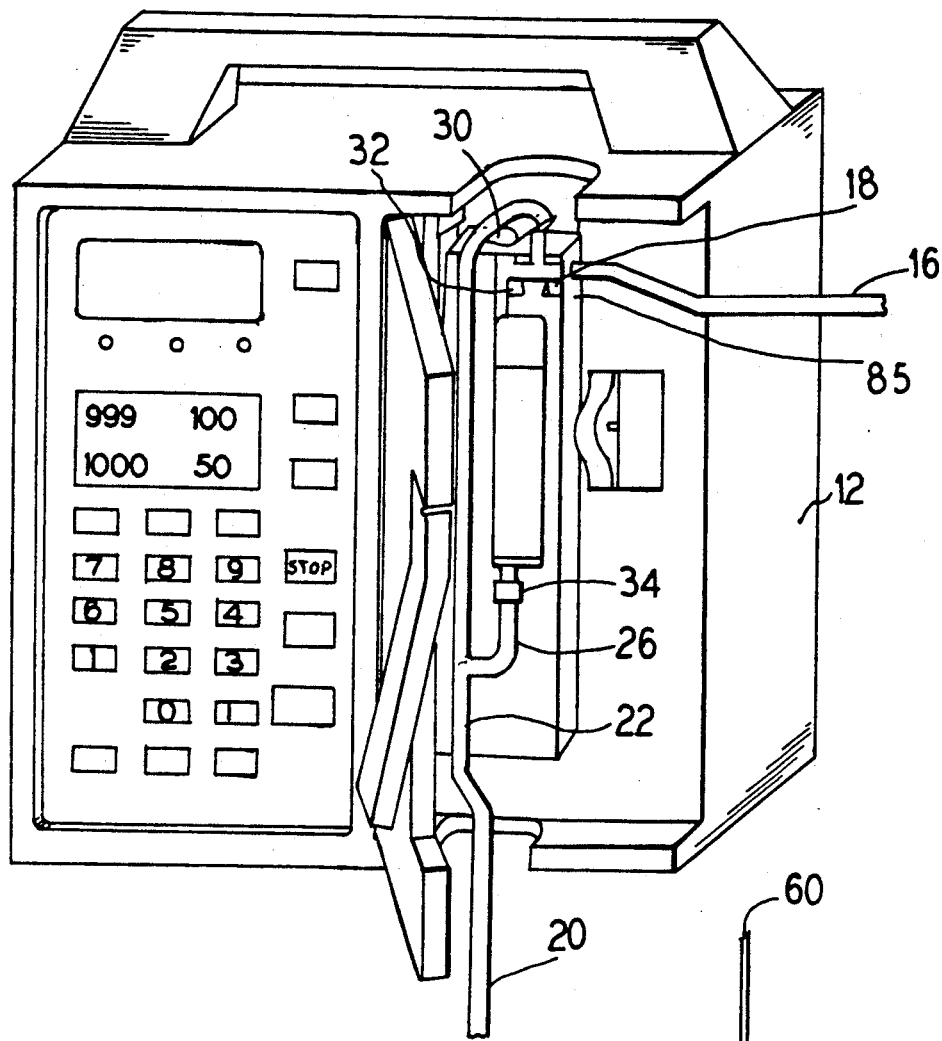
FIG. 5 illustrates a perspective view of an embodiment of the system of the present invention located within a pump.

FIG. 5 illustrates how the system is contained within the pump. To this end, a cassette 85 is provided. When so contained, the access member 30 is accessible for allowing a vial 42 to be coupled to the access member 30.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim as our invention:

1. A system for adding a beneficial agent to a fluid to be administered to a patent comprising:

a vial including an agent;

a fluid source coupled to a first fluid line;

an access member including means for coupling the vial to the access member and providing at least two separate fluid paths between the access member and an interior of the vial;

means for establishing fluid communication between the first fluid line and the access member;

the access member including means for allowing fluid to enter the vial from a first fluid path and allowing air to be vented from the vial through a second fluid path;

the access member also including means for allowing fluid to enter the vial through the second fluid path and exit the vial through the first fluid path;

the access member includes an adapter for allowing fluid to enter the vial including a rigid cannula having an inlet and a outlet and a shell spaced from said cannula intermediate of said cannula inlet and said cannula outlet, with said cannula and said shell defining a channel therebetween about the exterior of said cannula;

a tubing segment coupled to the access member for allowing fluid exiting the vial to be administered to a patient; and a pump that acts on a portion of the first fluid line.

2. The system of claim 1, including at least one valve for regulating fluid flow through at least a portion of the system.

3. The system of claim 1, including a filter located at an end of the access member.

4. A system for adding a beneficial agent to a fluid to be administered to a patent comprising:

a vial including an agent;

a fluid source coupled to a first fluid line;

an access member including means for coupling the vial to the access member and providing at least two separate fluid paths between the access member and an interior of the vial;

means for establishing fluid communication between the first fluid line and the access member;

the access member including means for allowing fluid to enter the vial from a first fluid path and allowing air to be vented from the vial through a second fluid path;

the access member also including means for allowing fluid to enter the vial through the second fluid path and exit the vial through the first fluid path;

a tubing segment coupled to the access member for allowing fluid exiting the vial to be administered to a patient;

a pump that acts on a portion of the first fluid line; and including four tubing segments and four valves for regulating the fluid flow through each segment.

5. The system of claim 1, wherein the means for establishing fluid communication between the first fluid line and the access member includes the tubing segment.

6. The system of claim , wherein the access member includes means for allowing air to enter the vial when fluid is drained from the vial.

7. The system of claim 1, wherein said channel includes a channel outlet short of said cannula inlet, wherein said channel outlet and said cannula inlet are both adaptable to pierce a single opening in the vial.

8. A system for adding a beneficial agent to a fluid to be administered to a patent comprising:

a vial including an agent;

a fluid source;

an access site for adding an agent to the fluid;

a first fluid pathway connected to the fluid source;

a second fluid pathway connected to the first fluid pathway and an end of the access site;

a third fluid pathway connected to an end of the access site;

a fourth fluid pathway, integral with the first fluid pathway, connected to an end of the third fluid pathway;

an adapter for allowing a vial to be coupled to the access site and establishing two fluid flow paths into and out of the vial;

a pump located between the first and fourth fluid pathway; and the system being so constructed and arranged that fluid flows into the vial from the second and third fluid pathway and out of the vial into the second fluid pathway.

9. The system of claim 8, wherein the access site includes a filter.

10. The system of claim 8, wherein the third fluid pathway is coupled to a filter that is coupled to the access site.

11. The system of claim 8, including four tubing segments and four valves for regulating fluid flow through each fluid pathway.

12. The system of claim 8, wherein the adapter includes a rigid cannula having an inlet and an outlet and a shell spaced from said cannula intermediate of said cannula inlet and said cannula outlet, with said cannula and said shell defining a channel therebetween, about the exterior of said cannula, said channel including a channel inlet short of said cannula outlet and a channel outlet short of said cannula inlet, wherein said channel outlet and said cannula inlet are both adaptable to pierce a single opening in the vial.

13. A system for adding a beneficial agent to a fluid to be administered to a patient comprising:

a vial including an agent;

a fluid source;

an access site for adding an agent to the fluid;

a first fluid pathway connected to the fluid source and a first valve for regulating fluid flow through the first fluid pathway;

a second fluid pathway connected to the first fluid pathway and an end of the access site and a second valve for regulating fluid flow through the second fluid pathway;

a third fluid pathway connected to an end of the access site and a fourth fluid pathway, and a third valve for regulating fluid flow through the third fluid pathway;

the fourth fluid pathway being integral with the first fluid pathway, and a fourth valve for regulating fluid flow through the fourth fluid pathway;

an adapter for allowing a vial to be coupled to the access site and establishing two fluid flow paths into and out of the vial; and a pump located between the first and fourth fluid pathways.

14. The system of claim 13, wherein the access site includes a filter.

15. The system of claim 13, wherein the third fluid pathway is coupled to a filter that is coupled to the access site.

16. The system of claim 13, wherein the adapter wherein includes a rigid cannula having an inlet and an outlet and a shell spaced from said cannula intermediate of said cannula inlet and said cannula outlet, with said cannula and said shell defining a channel therebetween, about the exterior of said cannula, said channel including a channel inlet short of said cannula outlet and a channel outlet short of said cannula inlet, wherein said channel outlet and said cannula inlet are both adaptable to pierce a single opening in the vial.

17. A method for delivering an agent to a patient comprising the steps of:

coupling a vial including the agent to a system for delivering fluid to a patient;

causing fluid to enter the vial, from an adaptor having at least two fluid paths that enter the vial and provide fluid communication between an access site and the vial, the fluid initially entering the vial from a first fluid path and air is vented from the vial from a second fluid path;

causing fluid to enter the vial from the second fluid path in the adaptor;

causing fluid to exit the vial from the first fluid path in the adaptor; and delivering the fluid that exits the vial to a patient.

18. The method of claim 17, wherein as fluid exits the vial air enters the vial from the second fluid path.

19. The method of claim 17, wherein fluid is caused to enter the vial through the first fluid path by gravity.

20. The method of claim 17, wherein a pump is used to cause at least some of the fluid to flow through at least one of the fluid flow paths.

21. The method of claim 17, including the steps of:
providing an air vent in the system; and
causing air exiting the vial to be vented through the air vent.

22. A method for reconstituting a drug comprising the steps of:
providing a fluid source coupled to a first fluid line;
providing a second fluid line, one end of which is in fluid with the first fluid line and a second end of which is in fluid communication with an access site;
providing a third fluid line, one end of which is in fluid communication with the first fluid line and a second end of which is connected to an end of the access site;
providing a pump that acts on a portion of the first fluid line;
providing first, second, third, and fourth valves, the first valve regulating fluid flow through the first tube upstream of the pump, the second valve regulating fluid flow within a portion of the second fluid line, the third valve regulating fluid flow within a portion of the third fluid line, and the fourth valve being located down stream of the pump and regulating fluid flow through a portion of the first fluid line downstream of the pump;
providing an adaptor including means for proving two fluid flow paths between a vial coupled to the adapter and the access side;
coupling a vial including a drug to be reconstituted to the adaptor;
closing the fourth valve while opening the first, second, and third valves and allowing fluid to fill the vial by gravity through a first fluid path;
closing the first and fourth valves while opening the second and third valves and causing the pump to act on the first tube segment to cause fluid to be pumped into the vial through a second fluid path;
closing the first and third valves and opening the second and fourth valves causing fluid to drain from the vial from the first fluid path; and
after the vial has drained closing the second and third valves and opening the first and fourth valves allowing fluid to be delivered from the fluid source.

23. The method of claim 22 wherein the valves and pump are sequenced to alternate delivery from the fluid source and the vial.

* * * * *